United States Patent [19]

Bidwell

[11] Patent Number: 5,328,476
[45] Date of Patent: Jul. 12, 1994

[54] ONE-TIME USE HYPODERMIC SYRINGE APPARATUS AND OPERATION THEREOF

[76] Inventor: James K. Bidwell, 1088 Bishop St., Suite 1224, Honolulu, Hi. 96813

[21] Appl. No.: 110,792

[22] Filed: Aug. 23, 1993

[51] Int. Cl.⁵ .............................................. A61M 5/00
[52] U.S. Cl. .................................. 604/110; 604/210; 604/218
[58] Field of Search ............... 604/110, 218, 187, 208, 604/209, 210

[56] References Cited

U.S. PATENT DOCUMENTS

| 4,840,616 | 6/1989 | Banks | 604/110 |
| 5,024,661 | 6/1991 | Wender et al. | 604/110 |
| 5,250,030 | 10/1993 | Corsich | 604/210 X |

Primary Examiner—John D. Yasko
Attorney, Agent, or Firm—Armstrong, Westerman, Hattori, McLeland & Naughton

[57] ABSTRACT

A hypodermic syringe apparatus having a plunger with first and second sets of grooves, and a casing having first and second lock members, such that when the plunger is fully inserted or reinserted into the casing, the plunger is prevented from being withdrawn relative to the casing. The first and second sets of grooves of the plunger have stepped portions, such that the plunger can be withdrawn relative to the casing when the plunger is positioned (position A) in such a way that the first set of grooves interacts with the first lock member of the casing; and such that the plunger can be inserted or reinserted into the casing when the plunger is positioned (position B) in such a way that the second set of grooves interacts with the second lock member of the casing.

4 Claims, 3 Drawing Sheets

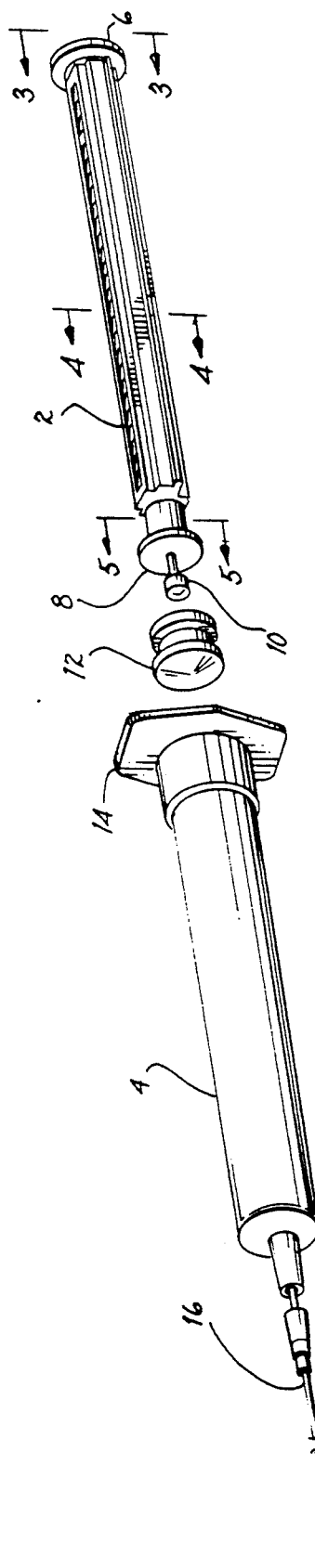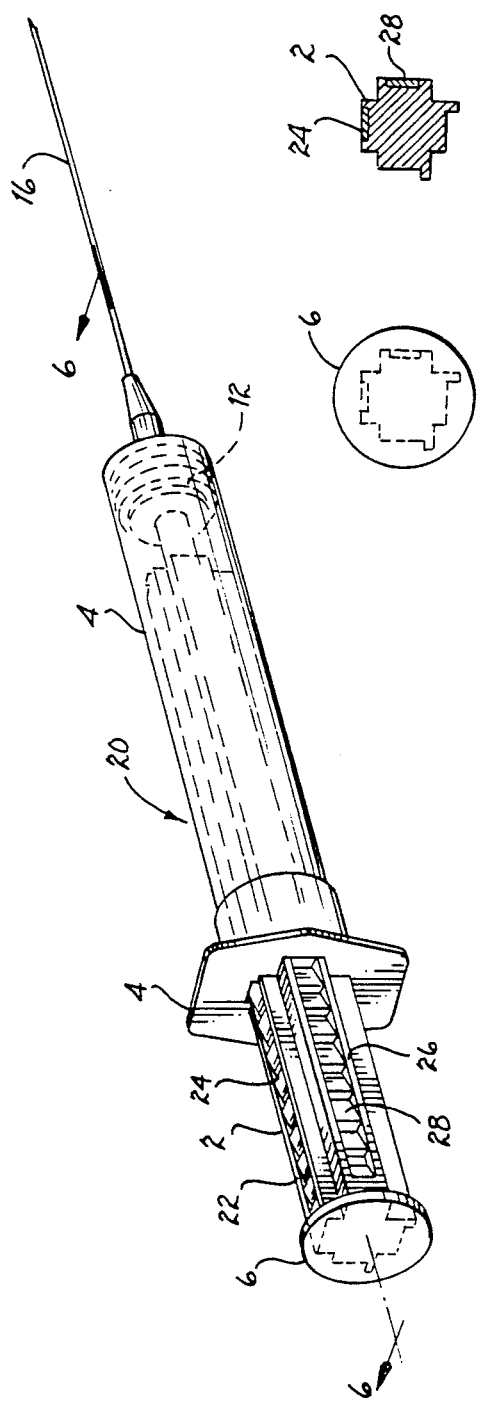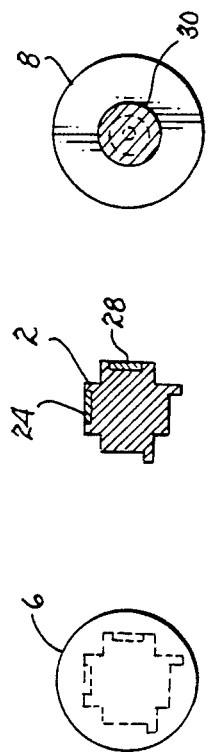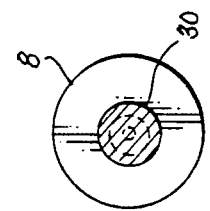

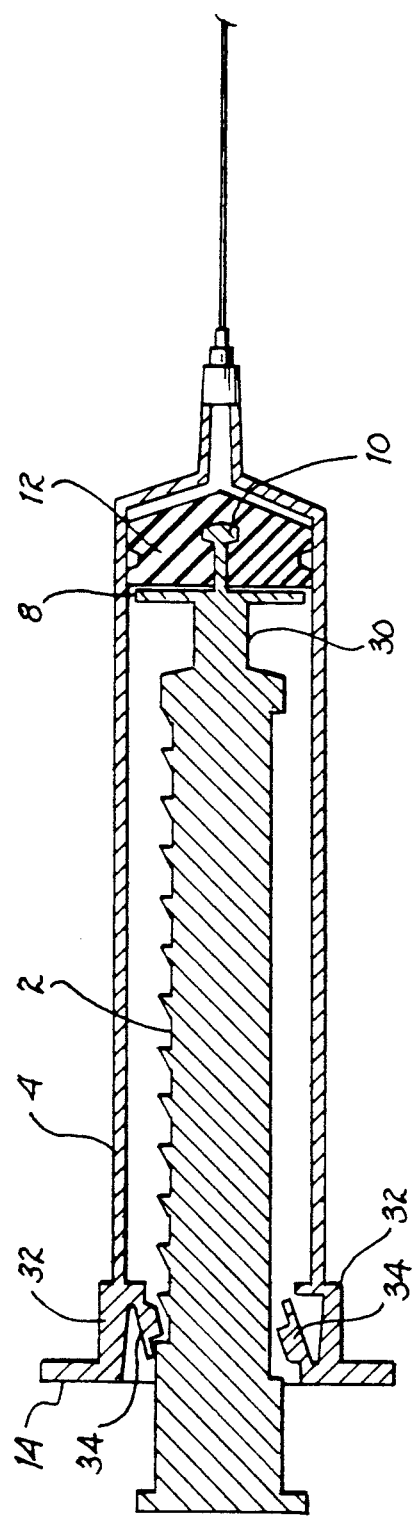
Fig. 6
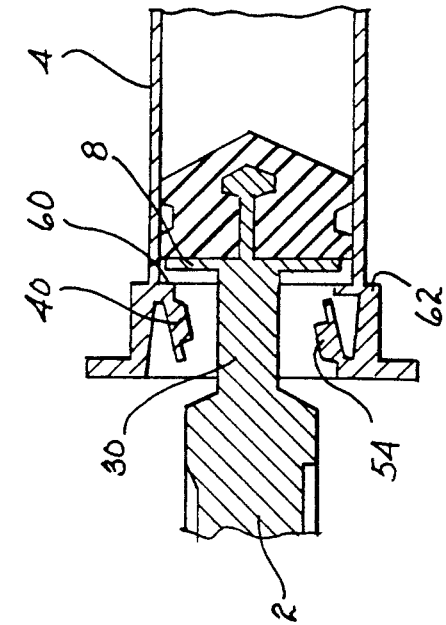
Fig. 9
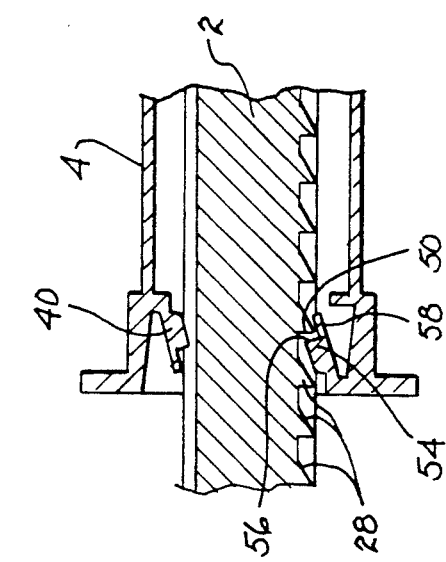
Fig. 8
Fig. 7

ONE-TIME USE HYPODERMIC SYRINGE APPARATUS AND OPERATION THEREOF

BACKGROUND OF THE INVENTION

1. Field of the Invention

This invention generally relates to a hypodermic syringe apparatus and operation thereof which is to be used only at one time; i.e., to be used for preventing the use of a hypodermic syringe apparatus for more than one time. The one-time use hypodermic syringe of this invention includes a plunger inserted within a casing such that when the plunger is withdrawn, medicine is loaded within the casing, and when the plunger is inserted or reinserted into the casing for injecting the medicine contained therein into a patient, the plunger thereafter cannot be withdrawn relative to the casing. The plunger locked in a position, for preventing withdrawal thereof relative to the casing, thereby prevents another user from using the syringe apparatus of this invention.

2. Description of the Relevant Art

A conventional syringe apparatus is known having a plunger and a casing which permits the plunger to inject medicine contained in the casing through a needle portion thereof into a patient, whereby the conventional syringe apparatus allows the plunger to be repeatedly withdrawn relative to the casing even upon insertion thereof. In other words, the conventional syringe apparatus can be re-used numerous times.

However, a syringe apparatus which can be re-used numerous times increases the risk of infecting not only another user, but the same user, especially if the syringe apparatus is left in an environment which can contaminate the syringe apparatus which may subsequently infect the same user for the repeated use thereof. Also, if another patient reuses the syringe apparatus, the risk is increased in infecting that user with an infectious disease of a previous user. Accordingly, a need was therefore felt to provide a one-time use hypodermic syringe so as to reduce or eliminate the above-discussed risks of infecting a user or patient.

It is therefore an object of the present invention to provide a one-time use hypodermic syringe.

It is another object of the present invention to provide a one-time use hypodermic syringe having a plunger and a casing, such that when the plunger has been fully inserted or reinserted into the casing, the plunger cannot thereafter be withdrawn relative to the casing.

It is still another object of the present invention to provide a one-time use hypodermic syringe, whereby the plunger has a plurality of groove portions, and a casing having lock portions corresponding to the groove portions of the plunger, such that the plunger is prevented from being withdrawn after insertion or reinsertion thereof into the casing.

It is a more particular object of the present invention to provide a one-time use hypodermic syringe having a plunger, whereby the groove portions include a first set of grooves having stepped portions thereof facing toward a front portion of the plunger, and a second set of grooves having stepped portions thereof facing a back portion of the plunger.

SUMMARY OF THE INVENTION

The aforementioned and other objects of the present invention are accomplished by providing the plunger with the first and second grooves, and the casing having the locked portions, such that when the plunger is fully inserted or reinserted into the casing, the plunger is prevented from being withdrawn relative to the casing. By providing the first and second sets of grooves having oppositely facing stepped portions on the plunger, the plunger can be withdrawn relative to the casing when the plunger is positioned (position A) such that the first set of grooves interacts with the locking portion of the casing; and the plunger can be inserted or reinserted into the casing when the plunger is positioned (position B) in such a way that the second set of grooves interacts with the locking portion of the casing.

These and other features of the invention will be understood upon reading of the following description along with the drawings.

BRIEF DESCRIPTION OF THE DRAWINGS

FIG. 1 is an exploded perspective view of a one-time use hypodermic syringe apparatus of this invention;

FIG. 2 is a perspective view of the one-time use hypodermic syringe of FIG. 1 shown in its fully assembled state;

FIG. 3 is a plan view taken in the direction of arrow 3—3 of FIG. 2 illustrating a pusher end portion of the plunger of the hypodermic syringe apparatus;

FIG. 4 is a cross-sectional view taken in direction of arrow 4—4 of FIG. 3 illustrating an intermediate portion of the plunger of the hypodermic syringe apparatus;

FIG. 5 is a cross-sectional view taken in the direction of arrow 5—5 of FIG. 2 illustrating a forward end portion of the plunger of the hypodermic syringe apparatus having a neck portion and a rubber end portion;

FIG. 6 is a cross-sectional view taken in the direction of arrow 6—6 of FIG. 2 illustrating the hypodermic syringe assembly having the plunger and a casing in a fully assembled state;

FIG. 7 is a cross-sectional view, taken along longitudinally, showing an intermediate portion of the fully assembled hypodermic syringe apparatus with the plunger at a position relative to the casing (position A) capable of being withdrawn, but incapable of being inserted or reinserted into the casing;

FIG. 8 is a cross-sectional view, taken along longitudinally, showing an intermediate portion of the fully assembled hypodermic syringe apparatus with the plunger at a position relative to the casing (position B) capable of being inserted or reinserted, but incapable of being withdrawn relative to the casing;

FIG. 9 is a cross-sectional view, taken along longitudinally, of the fully assembled hypodermic syringe apparatus, wherein the plunger is fully withdrawn and at a position capable of being turned, preferably at a 90° angle, relative to the casing for insertion or reinsertion into the casing;

DESCRIPTION OF THE PREFERRED EMBODIMENTS

Figure 10A:
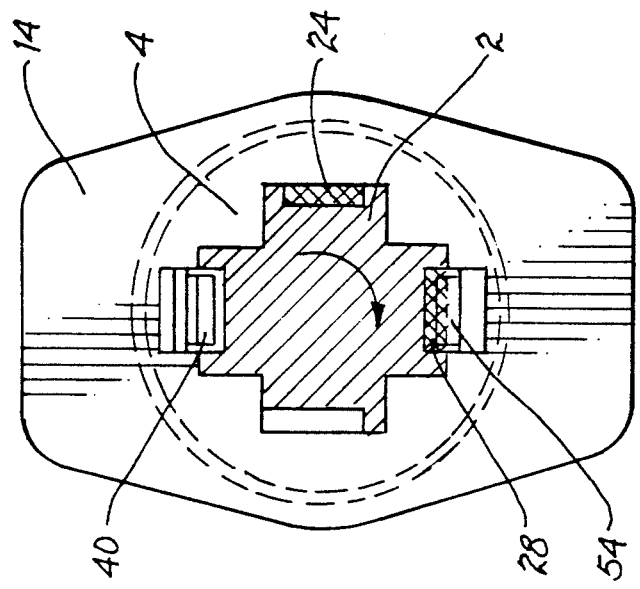
FIGS. 10A and 10B show cross-sectional views, each taken in a transverse direction, illustrating the relationship between the sets of grooves of the plunger and the locking portion of the casing when the plunger is at a position (position A, FIG. 10A) capable of being withdrawn relative to the casing; and thereafter, rotated in a direction shown in the arrow, when at a full retraction, to a position (position B, FIG. 10B) capable of being inserted or reinserted into the casing.

FIG. 1 is an exploded perspective view of the one-time use hypodermic syringe apparatus having a plunger 2 and a casing 4. The plunger 2 preferably has a pusher end member 6 attached at a rear end portion thereof; and a support member 8 and a holder member 10 at a front end portion thereof for supporting, and holding, respectively, a rubber member 12. The casing 4 preferably has a lock support member 14 at a rear end portion thereof, and a needle member 16 at a front end portion thereof.

As shown in the fully assembled state, as illustrated in FIG. 2, the one-time use hypodermic syringe apparatus, generally designated by reference number 20, has the rubber portion 12 held and supported by the support member 8 and the holder member 10 of the plunger 2 (see, also, FIG. 6).

As further shown in FIG. 2, the plunger further has, on a first side 22 thereof, a first set of grooves 24, and, on a second side 26 thereof, a second set of grooves 28. The directions in which the first side 22 and the second side 26 face are preferably perpendicular from each other.

FIG. 3 illustrates a plan view taken in direction of arrow 3—3 of FIG. 2 showing the pusher end member 6 of the plunger 2. FIG. 4 illustrates a cross-sectional view taken in the direction of arrow 4—4 of FIG. 3 showing an intermediate portion of the plunger 2, while FIG. 5 illustrates a plan view shown in the direction of arrow 5—5 of FIG. 2 showing the support member 8 capable of supporting the rubber member 12.

Illustrated in FIG. 6 is the plunger 2 substantially inserted or reinserted into the casing 4. Also, illustrated in FIG. 6 is the rubber member 12 fully held by the holder member 10, and fully supported by the support member 8. Preferably, the plunger 2 further includes a neck portion 30 adjacent the support member 8. Further-illustrated in FIG. 6 is a lock support member 14, and a lock holder member 32 located at a rear end portion of the casing 4. The lock holder member 32 has, preferably integral thereto, inwardly protruding lock members 34. The lock members 34 are preferably two in number, and located opposed from each other, as shown.

FIGS. 7 and 8 show the relationships between the first and second sets of grooves 24, 28, and the lock members 34. More particularly, FIG. 7 shows the plunger 2 partially withdrawn relative to the casing 4. Here, the first set of grooves 24 of the plunger 2 is shown interacting with one of the lock members 34 (a first lock member 40). As clearly shown in FIG. 7, each of the first set of grooves 24 has a stepped portion 42 facing the front portion of the hypodermic syringe apparatus 20 (i.e., in the direction towards the needle member 16 of the casing 4). The first lock member 40 preferably has a lock face portion 45 which substantially faces towards the rear end portion of the hypodermic syringe apparatus 20 (i.e., in the direction towards the pusher end member 6). The lock member 40 further includes a support portion 48 so as to support or stabilize the engagement of the face portion 45 of the first lock member 40 with the stepped portion 42 of one of the grooves of the first set of grooves 24.

With this structural arrangement, shown in FIG. 7, the face portion 45 of the first lock member 40 directly abuts the stepped portion 42 of one of the grooves of the first set of grooves 24 of the plunger 2; thereby, preventing the plunger 2 from being inserted or reinserted into the casing 4.

In FIG. 8, each of the grooves of the second set of grooves 28 of the plunger 2 also includes a stepped portion 50 which faces towards the rear end portion of the hypodermic syringe apparatus 20. A second lock member 54, opposite the first lock member 40, is further held by the lock holder member 32 and extends substantially inwardly towards the inner portion of the cylinder 4. The second lock member 54 includes a face portion 56 which faces towards the front end portion of the hypodermic syringe apparatus 20. With the structural arrangement, illustrated in FIG. 8, the face portion 56 of the second lock member 54 directly abuts against the stepped portion 50 of one of the grooves of the second set of grooves 28 so as to prevent the plunger from being withdrawn relative to the casing 4. The lock member 54 further includes a support portion 58 so as to support or stabilize the engagement of the face portion 56 of the second lock member 54 with the stepped portion 50 of one of the grooves of the second set of grooves 28.

As illustrated in FIG. 9, when the plunger 2 is fully withdrawn relative to the casing 4, the complete removal of the plunger 2 from the casing 4 is prevented by base portions 60, 62 of the first lock member 40 and the second lock member 54, respectively, by having these base portions 60, 62 directly abut the support member 8 of the plunger 2. More importantly, when the plunger 2 is at a position relative to the casing 4 (i.e., the plunger being fully retracted relative to the casing 4), as illustrated in FIG. 9, the first and second lock members 40, 54 of the casing 4 do not interact with the first and second sets of grooves 24, 28 of the plunger 2. Instead, the lock members 40, 54 are adjacent to the neck portion 30 of the plunger 2; thereby, freeing the first and second lock members 40, 54 from engagement with the sets of grooves 24, 28. Consequently, the plunger 2 can be rotated relative to the casing 4, as more fully discussed below in relation to the operation of the hypodermic syringe apparatus 20.

As to the operation of the hypodermic syringe apparatus 20, as previously discussed with respect to FIG. 9, when the plunger 2 is fully retracted relative to the casing 4, medicine (not shown) is accommodated within the casing 4. In the position of the plunger 2, at a full retraction relative to the casing 4, the first and second lock members 40, 54 are freed from interacting with the first and second lock members 40, 54 to thereby allow the plunger 2 to be rotated relative to the casing 4.

Figure 10B:
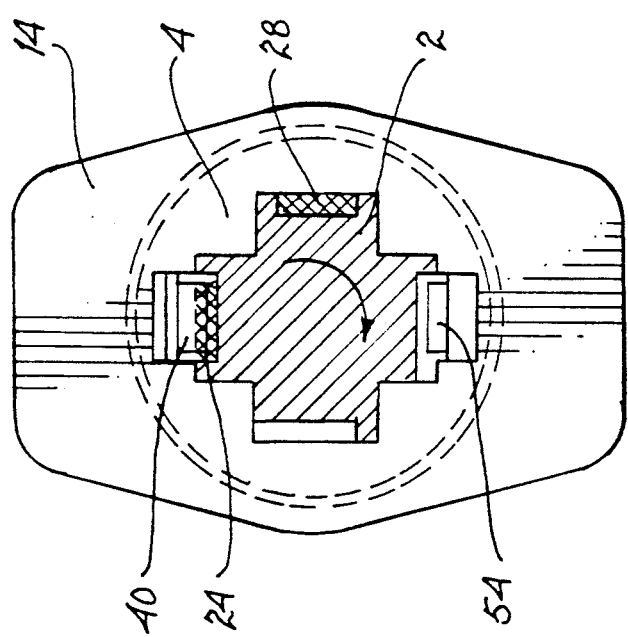

FIGS. 10A and 10B show the relative positions of the first and second sets of grooves 24, 28 with the first and second lock members 40, 54.

As more particularly illustrated in FIG. 10A, when the plunger 2 is at a position (position A) relative to the casing 4, the plunger 2 can be withdrawn relative to the casing 4 so that when the plunger is at a position illustrated in FIG. 9 (i.e., a full retraction of the plunger 2 relative to the casing 4), the plunger can be rotated, preferably by 90° (see, FIG. 10A) for allowing the plunger 2 to be at a position (position B), as illustrated in FIG. 10B, for consequently allowing the plunger 2 to be inserted or reinserted into the casing (see also, FIG. 8).

The above description is included to illustrate the preferred embodiments and the operations thereof, and is not intended to limit the scope of the invention. The scope of the invention is to be limited only by the following claims. From the above discussion, many variations are apparent to one skilled in the art which would yet be encompassed by the spirit and scope of the invention.

What is claimed is:

1. A one-time use hypodermic syringe apparatus, comprising:
   a casing, having a needle portion attached at a forward end thereof, for accommodating therein medication to be extracted through said needle; and
   a plunger accommodated within said casing and movable along a length of said casing,
   wherein said casing comprises first lock means, and said plunger comprises a second lock means for interacting with said first lock means of said casing for preventing, at a first position of the plunger relative to said casing, the plunger from being inserted or reinserted into said casing and for preventing, at a second position of the plunger relative to said casing, the plunger from being withdrawn relative to the casing,
   wherein said second lock means of said plunger comprises a first set of grooves on a first face of said plunger, and a second set of grooves on a second face of said plunger, wherein said first face and second face are directed perpendicular from each other,
   wherein said first set of grooves of said plunger includes stepped portions substantially facing towards a front end portion of said syringe apparatus, said front end portion of said syringe apparatus containing said needle portion of said casing, and
   wherein said second set of groves includes stepped portions substantially facing towards a rear end portion of said syringe apparatus, said rear end portion of said syringe apparatus containing a pusher portion of said plunger.

2. The one-time use hypodermic syringe apparatus as set forth in claim 1, wherein said first lock means of said casing comprises lock members oppositely located from each other and protruding inwardly towards an inside portion of said casing.

3. A method of using a hypodermic syringe apparatus for only one time, comprising the steps of:
   locking a plunger so as to prevent said plunger from being inserted or reinserted into a casing, said casing having a first lock means, and said plunger having a second lock means;
   retracting said plunger, to a substantially full extent relative to said casing, so as to fill up said casing with medication;
   rotating said plunger relative to said casing;
   unlocking said plunger so as to allow insertion or reinsertion thereof into said casing;
   reinserting said plunger into said casing so as to deliver said medication out from said casing; and
   locking said plunger so as to prevent said plunger from being withdrawn relative to said casing,
   wherein said steps of locking comprises the steps of interacting said first and second lock means, wherein said second lock means of said plunger comprises a first set of grooves on a first face of said plunger, and a second set of grooves on a second face of said plunger, wherein said first face and second face are directed perpendicular from each other, wherein said first set of grooves of said plunger includes stepped portions substantially facing towards a front end portion of said syringe apparatus, said front end portion of said syringe apparatus containing said needle portion of said casing, and wherein said second set of grooves includes stepped portions substantially facing towards a rear end portion of said syringe apparatus, said rear end portion of said syringe apparatus containing a pusher portion of said plunger.

4. The method as set forth in claim 3, wherein said step of rotating said plunger comprises the step of rotating said plunger at substantially 90° relative to said casing.

* * * * *